US 6,696,064 B2

(12) United States Patent
Youle et al.

(10) Patent No.: US 6,696,064 B2
(45) Date of Patent: Feb. 24, 2004

(54) METHODS OF PROTECTING VASCULATURE FROM DAMAGE BY DIPHTHERIA TOXIN-AND PSEUDOMONAS TOXIN-BASED IMMUNOTOXINS DURING THERAPY

(75) Inventors: Richard J. Youle, Chevy Chase, MD (US); Naoshi Hagihara, Saga (JP)

(73) Assignee: The United States of America as represented by the Department of Health and Human Services, Washington, DC (US)

( * ) Notice: Subject to any disclaimer, the term of this patent is extended or adjusted under 35 U.S.C. 154(b) by 0 days.

(21) Appl. No.: 09/884,695

(22) Filed: Jun. 19, 2001

(65) Prior Publication Data

US 2002/0016335 A1 Feb. 7, 2002

Related U.S. Application Data

(60) Provisional application No. 60/212,909, filed on Jun. 20, 2000.

(51) Int. Cl.[7] .......................... A61K 39/02; A61K 39/05; A61K 39/108; A61K 31/00; A01N 61/00
(52) U.S. Cl. ................................ 424/234.1; 424/236.1; 424/245.1; 424/260.1; 514/1; 514/2
(58) Field of Search ........................... 424/236.1, 234.1, 424/245.1, 260.1; 514/1, 2

(56) References Cited

U.S. PATENT DOCUMENTS 6,207,646 B1 * 3/2001 Krieg et al.

OTHER PUBLICATIONS

Laske et al. (J Neurosurg 1994 vol. 80 pp. 520–526).*
Laske et al. (Nat Med 1997 vol. 3 pp. 1362–1368).*
Leppla et al. (J Biol Chem 1980 vol. 255 pp. 2247–2250).*
Hagihara et al (Cancer Research vol. 60 pp 230–234), Jan. 2000.*

* cited by examiner

*Primary Examiner*—Mark Navarro
(74) *Attorney, Agent, or Firm*—Townsend and Townsend and Crew LLP

(57) ABSTRACT

Vascular damage has proven to be dose limiting in administering immunotoxins into the brain to treat brain tumors. Vascular toxicity of immunotoxins which rely in part on exposure to lowered pH in cellular endosomes and lysosomes can be avoided by administering an endosome pH-raising agent systemically during some or all of the time that the immunotoxin is present in the brain of the organism. Suitable endosome pH-raising agents include lysosomotrophic amines, proton ionophores, and vacuolar H+ ATPase inhibitors. The invention increases the therapeutic window of the immunotoxins and increases the likelihood the treatment will have an effect on the course of the tumor.

48 Claims, 1 Drawing Sheet

US 6,696,064 B2

METHODS OF PROTECTING VASCULATURE FROM DAMAGE BY DIPHTHERIA TOXIN-AND PSEUDOMONAS TOXIN-BASED IMMUNOTOXINS DURING THERAPY

CROSS-REFERENCES TO RELATED APPLICATIONS

This application claims the benefit of U.S. Provisional Patent Application Serial No. 60/212,909, filed Jun. 20, 2000, the contents of which are incorporated by reference for all purposes.

STATEMENT AS TO RIGHTS TO INVENTIONS MADE UNDER FEDERALLY SPONSORED RESEARCH AND DEVELOPMENT

Not applicable.

BACKGROUND OF THE INVENTION

The prognosis of patients with malignant brain tumors is poor. Standard therapy, including surgery, radiation, and chemotherapy has proven ineffective in the majority of cases. One attempt to improve this grim clinical outlook has resulted from the discovery that many brain tumors over express the transferrin ("Tf") receptor ("Tf-R"). A Tf-targeted immunotoxin known as Tf-CRM107 (Johnson, V. G. et al., *J. Biol Chem.*, 263:1295–1300 (1988)), a conjugate of transferrin ("Tf") and a mutant diphtheria toxin ("DT") lacking receptor-binding function (Greenfield, L. et al., *Science*, 238:536–539 (1987), can target and kill cells expressing Tf-R, such as tumor cells The potential of Tf-CRM107 for brain tumor therapy has been explored in vitro (Johnson, V. G. et al., *J. Biol Chem.*, 263:1295–1300 (1988), in animal models (Laske, D. W. et al., *J. Neurosurg.*, 80:520–526 (1994)), and in patients with malignant gliomas (Laske, D. W. et al., *Nat. Med.*, 3:1362–1368 (1997) (hereafter, "Laske 1997"). When delivered by high-flow (4–10 µl/min) interstitial microinfusion convection-enhanced delivery ("CED") (Bobo, R. H. et al., *Proc. Natl. Acad. Sci. USA*, 91:2076–2080 (1994)), intratumoral infusion of Tf-CRM107 in patients with malignant brain tumors produces tumor responses (Laske 1997). When CED is used, Tf-CRM107 (140 kDa) is distributed preferentially into the interstitial space of the tumor and the surrounding brain infiltrated by tumor and circumvents the blood-brain barrier ("BBB").

One factor limiting the success of Tf-CRM107 therapy is the fact that capillary endothelial cells in the brain express low levels of Tf-R (Jeffries, W. A. et al., *Nature*, 312:162–163 (1984)). A portion of patients receiving high doses of Tf-CRM107 display neurological deficits consistent with endothelial damage. MRI in these patients has revealed changes in the brain consistent with microvascular occlusion and/or petechial hemorrhage (Laske 1997). This vascular damage therefore limits the doses at which Tf-CRM107, and other immunoconjugates using Tf as a targeting agent, can be administered.

Lysosomotrophic amines, such as chloroquine, are used clinically to treat malaria and certain collagen diseases. These drugs accumulate in lysosomes and increase and neutralize vesicular pH (Kim, K., and Groman, N. B., *J. Bacteriol.*, 90:1552–1556 (1965)). DT enters the cell to inhibit protein synthesis, using the low pH of endosomes and lysosomes to trigger transport into the cytosol (Sandvig, K., and Olsnes, *J. Biol. Chem.*, 256:9068–9076 (1981); Donovan, J. J. et al., *Proc. Natl. Acad. Sci. USA*, 78:172–176 (1981); Sandvig, K., and Olsnes, S., *J. Cell Biol.*, 87:828–832 (1980); Draper, R. K., and Simon, M. I., *J. Cell Biol.*, 87:849–854 (1980). Thus, in vitro, chloroquine blocks the cytotoxicity of DT (Leppla, S. et al., *J. Biol. Chem.,* 255:2247–2250 (1980)), and presumably that of Tf-CRM107, whose toxicity arises from the same mechanism.

Unfortunately, the very benefit that chloroquine confers—blocking of the toxicity of Tf-CRM107—also renders its use problematic in connection with Tf-CRM107 cancer therapy. The clinical utility of Tf-CRM107 is its toxicity to the target tumor cells. Therefore, if chloroquine or a like agent is co-administered with Tf-CRM107 or other immunotoxins for which lowered endosomal pH is part of the process which activates their cytotoxic function, it can be expected that the chloroquine or other agent will render the tumor cells resistant to the toxic effects of the immunotoxin, thereby reducing the desired therapeutic effect.

SUMMARY OF THE INVENTION

The invention provides methods of decreasing toxicity to a vascular endothelial cell of immunotoxins used to treat brain tumors and residual cancer cells following surgical removal of a brain tumor. The immunotoxin is administered to the brain, and contacts the ablumenal surface of the vascular endothelial cell. The method comprises contacting the lumenal surface, but not the ablumenal surface, with an endosome pH-raising agent in an amount sufficient to protect the cell from toxic effects of the immunotoxin. The endosome pH-raising agent is selected from the group consisting of a lysosomotrophic amine, a proton ionophore, and a vacuolar H+ ATPase inhibitor. The lysosomotrophic amine can be, for example, chloroquine, hydrochloroquine, mefloquine, or a congener of chloroquine. The proton ionophore can be monensin. The vacuolar H+ ATPase inhibitor can be bafilomycin A. The contacting can occur in vivo.

The immunotoxin used in the method can comprise a toxic moiety selected from the group consisting of a mutated Pseudomonas exotoxin (PE) and a mutated diphtheria toxin (DT). Where a mutated PE is chosen as the toxic moiety, preferred forms of the PE are PE4E, PE35, PE38, and PE40. Where a mutated DT is chosen as the toxic moiety, it can be a diphtheria toxin with a deletion of all or some of the native receptor-binding domain, which results in reduced non-specific binding or toxicity compared to wild-type DT, a diphtheria toxin with a substitution of an amino acid for serine at position 508 which results in reduced non-specific binding or toxicity compared to wild-type DT, a diphtheria toxin with a substitution of an amino acid for serine at position 525 which results in reduced non-specific binding or toxicity compared to wild-type DT, and a diphtheria toxin with a substitution of an amino acid other than serine for serine at position 508 and of an amino acid other than serine for serine at position 525, which substitutions result in reduced non-specific binding or toxicity compared to wild-type DT. In some preferred forms, the DT deletion mutant of the native receptor-binding domain can commence at an amino acid residue selected from residue 388 and residue 389. In a particularly preferred embodiment, the mutated DT is one in which the serine at position 525 is replaced with a phenylalanine (the DT so mutated is known as "CRM107"). A preferred immunotoxin is Tf-CRM107.

In preferred embodiments, the vascular endothelial cell is in the brain of a mammal. In particularly preferred embodiments, the mammal is a human. In preferred embodiments, the immunotoxin is administered directly into the brain and the endosome pH-raising agent is administered systemically. In the most preferred method, the immunotoxin is Tf-CRM107 and the endosome pH-raising agent is chloroquine.

In another set of embodiments, the invention provides methods of decreasing toxicity of an immunotoxin administered into a brain to a vascular endothelial cell in the brain, the methods comprising systemically administering an endosome pH-raising agent in an amount sufficient to decrease toxicity of the immunotoxin to the vascular endothelial cell. The endosome pH-raising agent can be a lysosomotrophic amine, a proton ionophore, or a vacuolar H+ ATPase inhibitor. The lysosomotrophic amine can be chloroquine, hydrochloroquine, mefloquine, or a congener of chloroquine. The proton ionophore is monensin. The vacuolar H+ ATPase inhibitor is bafilomycin A.

The toxic moiety can be a mutated Pseudomonas exotoxin (PE) or a mutated diphtheria toxin (DT). Where a PE based immunotoxin is used, the toxic moiety can be PE4E, PE35, PE38, and PE40. Where a DT-based immunotoxin is employed, the toxic moiety can be selected from a diphtheria toxin with a deletion of all or some of the native receptor-binding domain which results in reduced non-specific binding or toxicity compared to wild-type DT, a diphtheria toxin with a substitution of an amino acid for serine at position 508 which results in reduced non-specific binding or toxicity compared to wild-type DT, a diphtheria toxin with a substitution of an amino acid for serine at position 525 which results in reduced non-specific binding or toxicity compared to wild-type DT, and a diphtheria toxin with a substitution of an amino acid other than serine for serine at position 508 and of an amino acid other than serine for serine at position 525, which substitutions result in reduced non-specific binding or toxicity compared to wild-type DT. Further, the deletion of the native DT receptor-binding domain can commence at an amino acid residue selected from residue 388 and residue 389. In a particularly preferred embodiment, the mutated DT is one in which the serine at position 525 is replaced with a phenylalanine (the DT so mutated is known as "CRM107"). A preferred immunotoxin is Tf-CRM107.

DETAILED DESCRIPTION

Introduction

Figure 1:
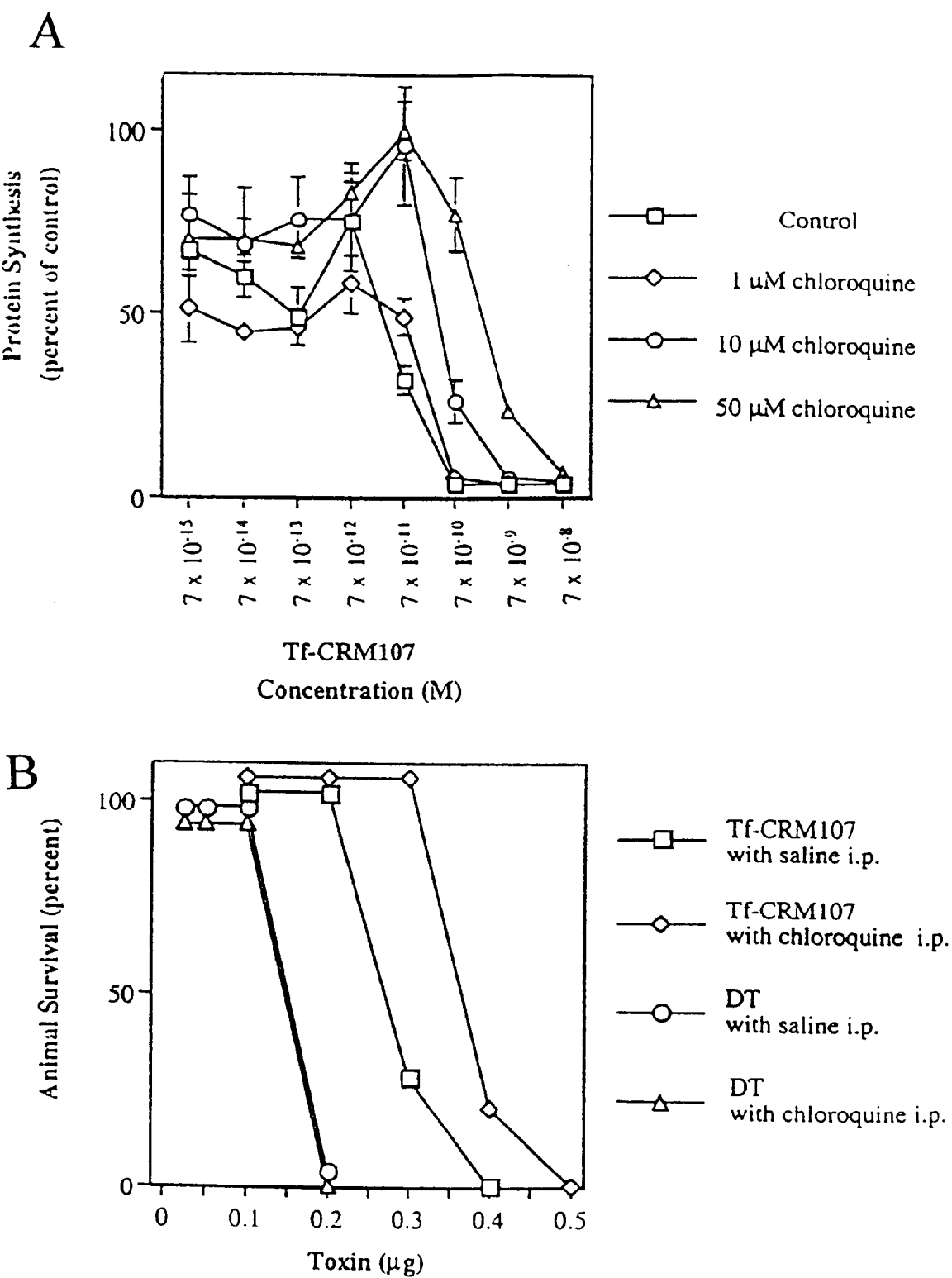
FIG. 1. A. Toxicity of Tf-CRM107 to U251MG human glioma cells after 12 h exposure with and without chloroquine (at 1, 10, and 50 μM). Chloroquine was added to cells 1 h before Tf-CRM107. Tf-CRM107 without chloroquine was used as the control. B. Survival rate after intracerebral injection of toxins into rats. Rats received injections in the right frontal lobe with the indicated dose of DT and Tf-CRM107. The percentage of survival of animals is shown (three to seven animals per group).

The present invention provides a solution to the problem of reducing the toxicity of diphtheria toxin- and Pseudomonas toxin-based immunoconjugates to brain vasculature without reducing the toxicity of the immunoconjugates to targeted brain tumor cells.

To place the invention in context, it may first be recalled that the blood-brain barrier ("BBB") functions to limit the diffusion of large molecules into, or out of, the brain, and thus provides a barrier to the entry into the brain not only of many therapeutic agents but also cells and proteins of the immune system. This barrier is in fact exploited in the use of Tf-CRM107 for therapy of brain cancers. As noted, Tf-CRM107 uses a mutated diphtheria toxin as its toxic moiety. The majorities of persons in the developed world are immunized against diphtheria, and in the systemic circulation, antibodies against diphtheria bind to, and therefore interfere with, the action of immunoconjugates, which, like CRM107, contain diphtheria toxin moieties. This immune response does not, however, interfere with treating brain tumors by administering Tf-CRM107 or other immunoconjugates directly into the brain. Since antibodies are large proteins (on the order of 150 kD), they cannot penetrate the BBB and are thus not available to bind to the immunoconjugate.

The present invention ingeniously couples one exploitation of the BBB to another. In the present invention, chloroquine, hydrochloroquine, or another agent, which raises endosomal pH, is administered systemically before, during or shortly after administration directly to the brain of a targeted toxin, which requires decreased endosomal pH to exert its toxic effects. The pH-raising agent, such as chloroquine, is chosen in part because it does not distribute to the brain in large amounts compared to that which remains in the systemic circulation or other compartments of the body. This permits the targeted toxin to exert its effect on the cells in the brain to which it is targeted with little or no interference from cells or proteins of the immune system, while at the same time, the pH-raising agent in the circulation acts on vascular endothelial cells from their lumenal side, thereby blocking the cytotoxicity of the toxin, without also crossing into the brain in quantities sufficient to render the targeted cells resistant to the immunotoxin.

Thus, the invention uses the concurrent administration of two agents whose action counters each other, one administered locally and one administered systemically, into two different body compartments. Whether this joint administration of two countering agents from two directions would work could not be predicted. While the effects of chloroquine on raising the pH of endosomes was known, it was unknown whether vascular endothelial cells would be able to absorb sufficient amounts of chloroquine from their lumenal surfaces to protect them from high local concentrations of immunotoxins infused directly at their ablumenal surfaces. Surprisingly, however, the invention demonstrates that two countering compounds, administered by two separate routes of administration, into two separate body compartments, increases the therapeutic window of one of the agents. This approach may be unique in therapeutic practice.

The present invention can be used with more than just CRM107 or other mutated diphtheria-based toxins. The lower pH of the endosome is also used by Pseudomonas exotoxin ("PE")-based toxins to aid the release of the toxic moiety into the cytosol. Based on the results herein, the administration of agents, which raise endosomal pH, such as lysosomotrophic amines and proton ionophores and vacuolar H+ ATPase inhibitors, will also protect vascular endothelial cells from the effects of PE-based immunotoxins. More generally, the results reported herein demonstrate that the invention can be used to protect the brain vasculature from the toxic effects of toxins, such as mutated diphtheria toxins and mutated Pseudomonas toxins, which require lowered endosomal pH to activate their toxicity in applications in which they are injected or infused directly into the brain. The invention increases the therapeutic window of such toxins, permitting higher does of those toxins to be used. The invention therefore affords a significant advance in the ability of practitioners to inhibit the growth and proliferation of brain tumors compared to the techniques previously available in the art.

Preferably, the method reduces toxicity of the immunotoxins to mammals by 20% or more, and more preferably by about 30% or more. Even more preferably, the reduction of toxicity is about 40%, 50%, 60%, 70%, or more. The extent of reduction of toxicity can be determined by, for example, the distress assays taught in the Examples, below. Finally, in view of our other work in which administration of immunotoxins into the brain in animal models has thus far been confirmed in human clinical trials, there is an expectation that the results found thus far in animal models will correlate to results in humans.

Definitions

Unless defined otherwise, all technical and scientific terms used herein have the meaning commonly understood by a person skilled in the art to which this invention belongs. The following references provide a general definition of many of the terms used in this invention: Singleton et al., DICTIONARY OF MICROBIOLOGY AND MOLECULAR BIOLOGY (2d ed. 1994); THE CAMBRIDGE DICTIONARY OF SCIENCE AND TECHNOLOGY (Walker ed., 1988); THE GLOSSARY OF GENETICS, 5TH ED., R. Rieger et al. (eds.), Springer Verlag (1991); and Hale & Marham, THE HARPER COLLINS DICTIONARY OF BIOLOGY (1991). Units, prefixes, and symbols are denoted in their Systeme International de Unites (SI) accepted form. Numeric ranges are inclusive of the numbers defining the range. Unless otherwise indicated, nucleic acids are written left to right in 5' to 3' orientation; amino acid sequences are written left to right in amino to carboxy orientation. The headings provided herein are not limitations of the various aspects or embodiments of the invention, which can be had by reference to the specification as a whole. Accordingly, the terms defined immediately below are more fully defined by reference to the specification in its entirety.

"Lysosomotrophic" agents are those which tend to accumulate preferentially in the lysosome. The endosome is an organelle, which evolves into a lysosome. Thus, agents who tend to accumulate in lysosomes are expected to also accumulate in endosomes. "Lysosomotrophic amines" are amines, which tend to accumulate preferentially in the lysosome.

An "ionophore" is a compound, which can carry specific ions through membranes of cells or organelles. A "proton ionophore" specifically carries protons and can equalize pH across membranes, for example, between an endosome and the cytosol of a cell.

A "vacuolar H+ ATPase" inhibitor inhibits the "pump" by which endosomes and lysosomes lower their pH.

As used herein, an "endosome pH-raising agent" is an agent which results in increasing the pH of an endosome or in preventing an endosome from decreasing pH. Examples of such agents are lysosomotrophic amines, proton ionophores, and vacuolar H+ ATPase inhibitors.

A "lumen" is defined as "[t]he space in the interior of a tubular structure, such as an artery or the intestine." Stedman's Medical Dictionary, Hensyl, ed., Williams & Wilkins, Baltimore, Md. ($25^{th}$ Ed., 1990), page 896.

Cells lining the lumen of blood vessels, such as the endothelial cells lining the vasculature of the brain, can be said to have a "lumenal" side, that is, the side facing the lumen, and an "ablumenal" side, that is, the side facing away from the lumen and, often, in contact with the cells of the organ or other structure through which the blood vessel passes.

"Polypeptide" refers to a polymer composed of amino acid residues, related naturally occurring structural variants, and synthetic non-naturally occurring analogs thereof linked via peptide bonds, related naturally occurring structural variants, and synthetic non-naturally occurring analogs thereof. Synthetic polypeptides can be synthesized, for example, using an automated polypeptide synthesizer. The term "protein" typically refers to large polypeptides. The term "peptide" typically refers to short polypeptides.

An "immunotoxin" is a molecule comprising a targeting molecule, such as an scFv, and a toxic moiety, such as a diphtheria toxin ("DT") or a Pseudomonas exotoxin ("PE") or cytotoxic fragment thereof.

A "targeting moiety" or "targeting molecule" is the portion of an immunoconjugate which has the ability to target the immunoconjugate to cells of interest. Typically, the targeting moiety is a ligand which binds to a specific receptor on a cell of interest, or an antibody, a scFv, a dsFv, a Fab, or a $F(ab')_2$ which recognizes a specific antigen on a cell of interest.

A "toxic moiety" is a cytotoxin or a portion of a cytotoxin which, when conjugated to a targeting moiety, either directly or through a peptide or other linker, renders the resulting immunotoxin cytotoxic to cells of interest.

"Fusion protein" refers to a polypeptide formed by the joining of two or more polypeptides through a peptide bond formed by the amino terminus of one polypeptide and the carboxyl terminus of the other polypeptide. A fusion protein may is typically expressed as a single polypeptide from a nucleic acid sequence encoding the single contiguous fusion protein. However, a fusion protein can also be formed by the chemical coupling of the constituent polypeptides.

The term "$IC_{50}$" refers to the concentration of a toxin or immunotoxin (expressed as ng/ml) required to inhibit protein synthesis by 50%.

The term "contacting" includes reference to placement in direct physical association.

"Conservative substitution" refers to the substitution in a polypeptide of an amino acid with a functionally similar amino acid. The following six groups each contain amino acids that are conservative substitutions for one another:

1) Alanine (A), Serine (S), Threonine (T);

2) Aspartic acid (D), Glutamic acid (E);

3) Asparagine (N), Glutamine (Q);

4) Arginine (R), Lysine (K);

5) Isoleucine (I), Leucine (L), Methionine (M), Valine (V); and

6) Phenylalanine (F), Tyrosine (Y), Tryptophan (W).

Two proteins are "homologs" of each other if they exist in different species, are derived from a common genetic ancestor and share at least 70% amino acid sequence identity.

Terms used to describe sequence relationships between two or more nucleotide sequences or amino acid sequences include "reference sequence," "selected from," "comparison window," "identical," "percentage of sequence identity," "substantially identical," "complementary," and "substantially complementary."

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters are used. Methods of alignment of sequences for comparison are well known in the art. Optimal alignment of sequences for comparison can be conducted, e.g., by the local homology algorithm of Smith & Waterman, *Adv. Appl. Math.* 2:482 (1981), by the homology alignment algorithm of Needleman & Wunsch, *J. Mol.*

Biol. 48:443 (1970), by the search for similarity method of Pearson & Lipman, Proc. Nat'l. Acad. Sci. USA 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection (see, e.g., *Current Protocols in Molecular Biology* (Ausubel et al., eds 1995 supplement)).

One example of a useful algorithm is PILEUP. PILEUP uses a simplification of the progressive alignment method of Feng & Doolittle, *J. Mol. Evol.* 35:351–360 (1987). The method used is similar to the method described by Higgins & Sharp, *CABIOS* 5:151–153 (1989). Using PILEUP, a reference sequence is compared to other test sequences to determine the percent sequence identity relationship using the following parameters: default gap weight (3.00), default gap length weight (0.10), and weighted end gaps. PILEUP can be obtained from the GCG sequence analysis software package, e.g., version 7.0 (Devereaux et al., *Nuc. Acids Res.* 12:387–395 (1984).

Another example of algorithms that are suitable for determining percent sequence identity and sequence similarity are the BLAST and the BLAST 2.0 algorithm, which are described in Altschul et al., *J. Mol. Biol.* 215:403–410 (1990) and Altschul et al., *Nucleic Acids Res.* 25:3389–3402 (1977)). Software for performing BLAST analyses is publicly available through the National Center for Biotechnology Information (http://www.ncbi.nlm.nih.gov/). The BLASTN program (for nucleotide sequences) uses as defaults a word length (W) of 11, alignments (B) of 50, expectation (E) of 10, M=5, N=−4, and a comparison of both strands. The BLASTP program (for amino acid sequences) uses as defaults a word length (W) of 3, and expectation (E) of 10, and the BLOSUM62 scoring matrix (see Henikoff & Henikoff, *Proc. Natl. Acad. Sci. USA* 89:10915 (1989)).

A "ligand" is a compound that specifically binds to a target molecule.

A "receptor" is compound that specifically binds to a ligand.

"Antibody" refers to a polypeptide ligand comprising at least a light chain or heavy chain immunoglobulin variable region which specifically binds and recognizes an epitope (e.g., an antigen). This includes intact immunoglobulins and the variants and portions of them well known in the art such as, Fab'$_2$ fragments, F(ab)' fragments, and scFv proteins. An scFv protein is a fusion protein in which a light chain variable region and a heavy chain variable region bound by a linker. Natural immunoglobulins are encoded by immunoglobulin genes. These include the kappa and lambda light chain constant region genes, the alpha, γ, delta, epsilon and mu heavy chain constant region genes, and the myriad immunoglobulin variable region genes. The term "antibody" includes polyclonal antibodies, monoclonal antibodies, chimeric antibodies and humanized antibodies, produced by immunization, from hybridomas, or recombinantly.

"Epitope" or "antigenic determinant" refers to a site on an antigen to which B and/or T cells respond. Epitopes can be formed both from contiguous amino acids or noncontiguous amino acids juxtaposed by tertiary folding of a protein. Epitopes formed from contiguous amino acids are typically retained on exposure to denaturing solvents whereas epitopes formed by tertiary folding are typically lost on treatment with denaturing solvents. An epitope typically includes at least 3, and more usually, at least 5 or 8–10 amino acids in a unique spatial conformation. Methods of determining spatial conformation of epitopes include, for example, x-ray crystallography and 2-dimensional nuclear magnetic resonance. See, e.g., *Epitope Mapping Protocols* in METHODS IN MOLECULAR BIOLOGY, Vol. 66, Glenn E. Morris, Ed (1996).

A ligand or a receptor "specifically binds to" a compound analyte when the ligand or receptor functions in a binding reaction which is determinative of the presence of the analyte in a sample of heterogeneous compounds. Thus, the ligand or receptor binds preferentially to a particular analyte and does not bind in a significant amount to other compounds present in the sample. For example, a polynucleotide specifically binds to an analyte polynucleotide comprising a complementary sequence and an antibody specifically binds under immunoassay conditions to an antigen analyte bearing an epitope against which the antibody was raised.

"Immunoassay" refers to a method of detecting an analyte in a sample in which specificity for the analyte is conferred by the specific binding between an antibody and a ligand. This includes detecting an antibody analyte through specific binding between the antibody and a ligand. See Harlow and Lane (1988) ANTIBODIES, A LABORATORY MANUAL, Cold Spring Harbor Publications, New York, for a description of immunoassay formats and conditions that can be used to determine specific immunoreactivity.

"Linker" refers to a molecule that joins two other molecules, either covalently, or through ionic, van der Waals or hydrogen bonds, e.g., a nucleic acid molecule that hybridizes to one complementary sequence at the 5' end and to another complementary sequence at the 3' end, thus joining two non-complementary sequences.

"Pharmaceutical composition" refers to a composition suitable for pharmaceutical use in a mammal. A pharmaceutical composition comprises a pharmacologically effective amount of an active agent and a pharmaceutically acceptable carrier. "Pharmacologically effective amount" refers to that amount of an agent effective to produce the intended pharmacological result. "Pharmaceutically acceptable carrier" refers to any of the standard pharmaceutical carriers, buffers, and excipients, such as a phosphate buffered saline solution, 5% aqueous solution of dextrose, and emulsions, such as an oil/water or water/oil emulsion, and various types of wetting agents and/or adjuvants. Suitable pharmaceutical carriers and formulations are described in REMINGTON'S PHARMACEUTICAL SCIENCES, 19th Ed. (Mack Publishing Co., Easton, 1995). Preferred pharmaceutical carriers depend upon the intended mode of administration of the active agent. Typical modes of administration include enteral (e.g., oral) or parenteral (e.g., subcutaneous, intramuscular, intravenous or intraperitoneal injection; or topical, transdermal, or transmucosal administration). A "pharmaceutically acceptable salt" is a salt that can be formulated into a compound for pharmaceutical use including, e.g., metal salts (sodium, potassium, magnesium, calcium, etc.) and salts of ammonia or organic amines.

A "subject" of diagnosis or treatment is a human or non-human mammal.

"Treatment" refers to prophylactic treatment or therapeutic treatment.

A "prophylactic" treatment is a treatment administered to a subject who does not exhibit signs of a disease or exhibits only early signs for the purpose of decreasing the risk of developing pathology.

A "therapeutic" treatment is a treatment administered to a subject who exhibits signs of pathology for the purpose of diminishing or eliminating those signs.

Toxins

The methods of the invention can be used with any toxins whose toxicity is dependent upon exposure to low pH in an endosome to function. In preferred embodiments, the toxins are bacterial protein toxins. Such proteins are well known in the art, and are discussed at length in such sources as Aloub, J. and Freer, J., eds., *The Comprehensive Sourcebook of Bacterial Protein Toxins*, Academic Press, Inc., San Diego, Calif. ($2^{nd}$ Ed., 1999).

In particularly preferred embodiments, the toxins are selected from mutated diphtheria toxin ("DT") and mutated Pseudomonas exotoxin ("PE") (the respective native, unmutated forms of these toxins are referred to herein as the "wildtype" form of the toxin). Pseudomonas exotoxin is an extremely active monomeric protein of 66 kD secreted by *Pseudomonas aeruginosa* which inhibits protein synthesis in eukaryotic cells through the enzymatic inactivation of Elongation Factor 2 ("EF-2") by catalyzing its ADP-ribosylation.

The structure of PE is well known, and consists of three structural domains. Domain Ia, amino acids 1–252, is responsible for cell binding. Domain II, amino acids 252–364, is responsible for translocation into the cytosol, and Domain III, amino acids 400–613, is responsible for inactivation of EF-2. The function of Domain Ib, amino acids 365–399, remains undefined. Some or all of Domain Ib can, however, be deleted without loss of cytotoxicity. A number of mutated forms of PE are known.

Frequently, Domain Ia of PE is deleted to eliminate the ability of the construct to bind to cells non-specifically, as taught in U.S. Pat. No. 4,892,827, although this can also be achieved, for example, by mutating certain residues of Domain I. U.S. Pat. No. 5,512,658, for instance, discloses that a mutated PE in which Domain I is present but in which the basic residues of Domain I at positions 57, 246, 247, and 249 are replaced with acidic residues (glutamic acid, or "E")) exhibits greatly diminished non-specific cytotoxicity. This mutant form of PE is sometimes referred to as PE4E.

Further, some or all of Domain 1b may be deleted, and the remaining portions joined by a linker or directly by a peptide bond. Some of the amino portion of Domain II may be deleted. And, the C-terminal end may contain the native sequence of residues 609–613 (REDLK), or may contain a variation found to maintain the ability of the construct to translocate into the cytosol, such as REDL or KDEL, and repeats of these sequences. See, e.g., U.S. Pat. Nos. 5,854,044; 5,821,238; and 5,602,095 and WO 99/51643. In preferred embodiments, the PE is PE4E, PE40, or PE38 (see, e.g., Pastan et al., Biochim. Biophys. Acta 1333:C1–C6 (1997)) or a 35 kD truncation of PE known in the art as PE35. Any form of PE in which non-specific cytotoxicity has been eliminated or reduced to levels in which significant toxicity to non-targeted cells does not occur, however, can be used in the methods of the present invention so long as it remains capable of translocation and EF-2 ribosylation upon exposure to lowered pH in an endosome. Thus, for example, the invention can be used with Tf-targeted PEs such as PE4E, PE38, and PE40 to reduce vascular damage when these immunotoxins are introduced into the brain.

In even more preferred embodiments, the toxin is a mutant form of diphtheria toxin ("DT"). DT is a protein secreted by toxigenic strains of Corynebacterum Diphtheriae. It is initially synthesized as a 535 amino acid polypeptide which undergoes proteolysis to form the toxin, which is composed of two subunits, A and B, joined by a disulfide bond. The B subunit, found at the carboxyl end, is responsible for cell surface binding and translocation; the A subunit, which is present on the amino end, is the catalytic domain, and causes the ADP ribosylation of Elongation Factor 2 ("EF-2"), thereby inactivating EF-2. Since EF-2 is essential for a cell to synthesize proteins, inactivation of the EF-2 in a cell causes its death. See generally, Uchida et al., Science 175:901–903 (1972); Uchida et al., J. Biol. Chem. 248:3838–3844 (1973).

In a preferred series of embodiments, the mutant form of DT is one in which is deficient in the cell binding function but not the cell translocation function. These include mutants in which the native receptor-binding domain, which comprises amino acid residues 384–535, is truncated or wholly removed, and mutants in which one or more residues critical for cell binding or translocation are mutated to residues which reduce or destroy the functionality of the domain.

Deletion mutants of the native receptor-binding domain currently in clinical trials include DT389, a DT in which the carboxyl terminal sequence beginning at residue 389 is removed (e.g., LeMaistre et al., Blood 91:399–405 (1999)), and a form truncated at residue 388. See, Hall et al., Leukemia 13:629–633 (1999). The domain can also be truncated commencing at other residues, such as 385, 386, 387, 390, or 391, or the entire domain, starting at residue 384, can be deleted. Mutants in which smaller portions of the domain are deleted can also be used, provided that they do not retain non-specific binding activity. The degree to which any particular truncation or other mutant retains non-specific binding can be readily measured by standard assays in the art, such as that taught by Vallera et al., Science 222:512–515 (1983).

In a preferred class of embodiments, the mutant DTs contain mutations at one or more residues of the native receptor-binding domain which reduce or eliminate binding of the molecule to the receptor. These include DT molecules which have mutations in the B subunit which result in reduced non-specific binding to cells, such as mutants CRM9, CRM45, CRM102, CRM103, and CRM107, as described, for example, by Nicholls and Youle in Frankel, ed., *Genetically Engineered Toxins*, Marcel Dekker, Inc., New York, N.Y. (1992).

In a particularly preferred embodiment, the mutated DT is CRM107. CRM107 contains an amino acid substitution of phenylalanine for serine at position 525, resulting in a more than 1000-fold reduction in cell binding, without affecting the translocating properties of the B subunit. The A subunit is unaffected and, when introduced into target cells, retains the full toxicity of native DT. Thus, CRM107 is particularly well suited for use as the toxic moiety, or component, of immunotoxins. It should be noted, however, that position 525 of DT was substituted with each of the natural amino acids and that a number of amino acids were found to result in reduced toxicity to cells (toxicity is usually reduced proportionately to binding of the toxin and can be used as an alternative measure). Thus, while the substitution of phenylalanine for serine resulted in the greatest reduction in toxicity, many of the other amino acid substitutions also reduced toxicity and could be used in the methods herein. Any particular substitution can of course be tested for non-specific toxicity to confirm whether it is suitable for use in the methods of the invention.

Other positions in the native receptor-binding domain can be mutated in place of or addition to position 525 to reduce or eliminate non-specific binding. For examples, position 508 can be mutated from serine to phenylalanine to reduce binding. While this mutation results in the greatest degree of loss of non-specific binding, however, other amino acid residue substitutions also reduce binding. Any particular substitution of another amino acid for the serine at position 508 can be tested to determine the degree to which it has lost the ability to bind non-specifically. Standard assays in the art, such as those taught by Vallera et al., supra, can be used for these determinations. Moreover, one can form a double mutant in which the serine at position 508 and in which the serine at position 525 are both mutated to decrease non-specific binding. In a preferred embodiment, the serine at position 508 and the serine at position 525 are both mutated to phenylalanine.

Formation of Immunotoxins

The formation of immunotoxins is well known in the art. Generally, a molecule with cytotoxicity, such as a mutated PE or DT, is coupled to a molecule which binds specifically to a desired target cell. This molecule is generally considered the targeting portion, or moiety, of the immunotoxin, while the toxic molecule is considered the toxic moiety. Formation of immunotoxins can be performed by chemical synthesis or, particularly where both the targeting moiety and the toxic moiety are polypeptides, by recombinant means.

Nucleic acid sequences encoding immunotoxins which can be used in the invention can be prepared by any suitable method including, for example, cloning of appropriate sequences or by direct chemical synthesis by methods such as the phosphotriester method of Narang, et al., *Meth. Enzymol.* 68:90–99 (1979); the phosphodiester method of Brown, et al., *Meth. Enzymol.* 68:109–151 (1979); the diethylphosphoramidite method of Beaucage, et al., *Tetra. Lett.* 22:1859–1862 (1981); the solid phase phosphoramidite triester method described by Beaucage & Caruthers, *Tetra. Letts.* 22(20):1859–1862 (1981), e.g., using an automated synthesizer as described in, for example, Needham-VanDevanter, et al. *Nucl. Acids Res.* 12:6159–6168 (1984); and, the solid support method of U.S. Pat. No. 4,458,066. Chemical synthesis produces a single stranded oligonucleotide. This may be converted into double stranded DNA by hybridization with a complementary sequence, or by polymerization with a DNA polymerase using the single strand as a template. One of skill would recognize that while chemical synthesis of DNA is limited to sequences of about 100 bases, longer sequences may be obtained by the ligation of shorter sequences.

Once expressed, the recombinant immunoconjugates, antibodies, and/or effector molecules of the present invention can be purified according to standard procedures of the art, including ammonium sulfate precipitation, affinity columns, column chromatography, and the like (see, generally, R. Scopes, PROTEIN PURIFICATION, Springer-Verlag, N.Y. (1982)). Substantially pure compositions of at least about 90 to 95% homogeneity are preferred, and 98 to 99% or more homogeneity are most preferred for pharmaceutical uses.

In addition to recombinant methods, immunotoxins can also be constructed in whole or in part using standard peptide synthesis. Solid phase synthesis of polypeptides of less than about 50 amino acids in length may be accomplished by attaching the C-terminal amino acid of the sequence to an insoluble support followed by sequential addition of the remaining amino acids in the sequence. Techniques for solid phase synthesis are described by Barany & Merrifield, THE PEPTIDES: ANALYSIS, SYNTHESIS, BIOLOGY. VOL. 2: SPECIAL METHODS IN PEPTIDE SYNTHESIS, PART A. pp. 3–284; Merrifield, et al. *J. Am. Chem. Soc.* 85:2149–2156 (1963), and Stewart, et al., SOLID PHASE PEPTIDE SYNTHESIS, 2ND ED., Pierce Chem. Co., Rockford, Ill. (1984). Proteins of greater length may be synthesized by condensation of the amino and carboxyl termini of shorter fragments. Methods of forming peptide bonds by activation of a carboxyl terminal end (e.g., by the use of the coupling reagent N, N'-dicycylohexylcarbodiimide) are known to those of skill.

The procedure for attaching a toxic molecule to a targeting molecule will vary according to the chemical structure of the toxic molecule. Polypeptides typically contain variety of functional groups; e.g., carboxylic acid (COOH), free amine (—$NH_2$) or sulfhydryl (—SH) groups, which are available for reaction with a suitable functional group on an antibody to result in the binding of the effector molecule. Alternatively, the targeting molecule is derivatized to expose or attach additional reactive functional groups. The derivatization may involve attachment of any of a number of linker molecules such as those available from Pierce Chemical Company (Rockford Ill.). Suitable linkers are well known to those of skill in the art and include, but are not limited to, straight or branched-chain carbon linkers, heterocyclic carbon linkers, or peptide linkers. Where the targeting molecule and the toxin molecule are polypeptides, the linkers may be joined to the constituent amino acids through their side groups (e.g., through a disulfide linkage to cysteine). However, in a preferred embodiment, the linkers will be joined to the alpha carbon amino and carboxyl groups of the terminal amino acids.

In the most preferred embodiment, CRM107 is coupled to transferrin to form Tf-CRM107. The creation of this immunotoxin is discussed in some detail in Johnson et al., J. Biol. Chem., 263:1295–1300 (1988)

Lysosomal pH-Raising Agents

DT enters the cell using the low pH of endosomes and lysosomes to trigger transport into the cytosol. See, e.g., Sandvig and Olsnes, J. Biol. Chem. 256:9068–9076 (1981); Donovan et al., Proc. Natl. Acad. Sci. USA 78:172–176 (1981); Draper and Simon, J. Cell Biol., 87:849–854 (1980). PE likewise requires a lower pH environment for activation. Thus, agents which can raise the pH of endosomes or prevent endosomes from lowering their pH block the ability of these toxins to kill cells.

The methods of the invention employ such agents. A variety of agents are known which either raise endosomal pH or which prevent endosomes from lowering their pH. These agents can be used in the methods herein, with two general provisos. First, the agents cannot be so toxic when administered systemically as to themselves cause serious and permanent injury to the organism to which they are administered. Because the methods of the invention are designed to inhibit the growth of gliomas and other tumors which are typically life-threatening and for which no better treatment is known, however, even agents with significant toxic side effects may be used, in the practitioner's discretion. Second, when administered systemically, the agent should cause an increase in endosomal pH in the endothelial cells lining the blood vessels of the brain without causing an equal increase in the pH of the endosomes of the cells of the brain. The pH of the endosomes of the endothelial cells should be at least 1 pH unit higher than that of the endosomes of the brain cells.

At least three classes of pH-raising agents are useful in the methods of the invention: lysosomotrophic amines, proton ionophores, and agents which block or which interfere with vacuolar H+ ATPase, the "pump" by which endosomes and lysosomes lower their pH. Lysosomotrophic agents, by definition, are those which accumulate or have an effect preferentially in the lysosome, and amines have the property of raising pH. Chloroquine and its related compounds, such as hydrochloroquine and mefloquine, are in this class, as are methylamine, ammonium chloride, cocaine and lidocaine. Proton ionophores, such as monensin, promote the transfer of protons across membranes and thus to equalize pH within the cell. This action prevents the endosome from lowering its pH. An example of the third group is an antibiotic, a vacuolar H+ ATPase inhibitor known as bafilomycin A.

For ease of use and cost, it is desirable that the particular agent chosen be one already approved for use in humans, although other agents can be tested for their clinical use if desired. Preferably, the agent chosen should also have a blood-brain barrier (BBB) permeability which is sufficiently low so that, when administered into the circulation, the amount of the agent reaching the brain is significantly lower than that which remains in the circulation or other body compartments. Additionally, when administered in amounts sufficient to protect vascular endothelial cells lining the brain from toxicity from PE- or DT-based immunotoxins administered to the ablumenal side of the cells, the amounts passing through the BBB into the brain should not be sufficient to protect the cells of the brain (specifically, the cells other than those of the vasculature serving the brain) from the toxicity of PE- or DT-based immunotoxins administered into the brain.

In preferred embodiments, the lysosomotrophic amine is chloroquine or hydrochloroquine. Chloroquine can be administered orally, in the form of chloroquine phosphate, or by injection or i.v., in the form chloroquine hydrochloride. Both are available commercially under the trademark ARALEN® from Sanofi Pharmaceuticals, Inc. (New York, N.Y.). See generally, *Physician's Desk Reference*, Medical Economics Company, Inc., Montvale, N.J. ($54^{th}$ Ed. 2000), at pp. 2733–2735. Chloroquine does distribute to the brain when administered, and is deposited there, but in amounts some 7 to 70 times smaller than those that are deposited in other body tissues. Thus, chloroquine can be administered in amounts sufficient to protect vasculature from brain-administered immunotoxins without also protecting brain cells targeted by those immunotoxins. This has been confirmed experimentally. As reported in the Examples below, a surrogate measure of chloroquine entry into the brain in a rat model indicated that the amount reaching the brain is insufficient to interfere with the effect of immunotoxins in the brain. This same test can be used to determine whether other lysosomotrophic amines are suitable for use in the invention.

Concerns that contrast-enhancing brain tumors might cause the BBB to leak, thus losing some its protective qualities, led us to examine whether enough chloroquine might enter the brain under such conditions to interfere with toxin efficacy with respect to target tumor cells. This hypothesis was tested using a "worst case scenario" animal model of leaky tumor vasculature. As set forth in the Examples, below, chloroquine retained its ability to protect vasculature without protecting targeted tumor cells from immunotoxins. It can thus be predicted that the growth of contrast-enhancing tumors can be inhibited by the practice of the invention.

Children should be given chloroquine orally since it is harder to control toxicity to them by parenteral administration. Where high doses are desired, for example, to counter especially high doses of immunotoxin, it may be preferable to use hydroxychloroquine since hydroxychloroquine may result in lower toxicity to the eyes than chloroquine. See, e.g., Tracy, J., and Webster, L., Jr., in Hardman and Limbird, eds., *Goodman & Gilman's The Pharmacological Basis of Therapeutics*, The McGraw-Hill Companies, Inc., New York, N.Y. ($9^{th}$ Ed. 1996) (hereafter "Goodman and Gilman"), pp. 965–985. Other congeners of chloroquine may also be used, with due attention to the contraindications and limitations on their use.

Methods of Administration

The methods of the invention contemplate administration of DT- and PE-based immunotoxins directly into the brain in the area of a tumor and, where possible, directly into a tumor. Administration into the brain or brain tumor can be performed by techniques conventional in neurosurgery, including stereotactic cannulation and visual observation followed by direct injection into sites around the site from which a tumor has been excised, to kill residual cells. Injection of immunotoxins to treat brain cancers is described in detail, for example, in Laske, D. W. et al., *Nat. Med.,* 3:1362–1368 (1997). Phase II clinical trials administering DT-based immunotoxin to brain tumors have been conducted at 10 hospitals around the United States, and clinical trials delivering PE-based immunotoxins have been conducted at additional hospitals or are underway.

In general, it is desirable to commence administration of the endosomal pH-raising agent shortly prior to administration of the immunotoxin and to continue administration as long as free immunotoxin is present. Preferably, the agent intended to protect the vascular endothelial cells is administered sufficiently in advance of the immunotoxin so that the pH of the endosomes of the cells is about 5.5 or higher at the time the immunotoxins are introduced. In most instances, this can be assumed to be the case if the agent has reached the desired concentration in the blood for at least one-half hour. If desired, however, the agent can be administered roughly simultaneously with the immunotoxin (particularly if the agent is administered by i.v.), or even shortly after the start of the administration of the immunotoxin.

While protecting the endothelial cells from the very start of the administration of the immunotoxin is desirable, the presence of the protective agent at any point in the process will be beneficial, even after administration of the immunotoxin has been concluded, so long as free immunotoxin is still present which might bind to a vascular endothelial cell. Moreover, it is desirable that the endosomal pH-raising agent is maintained at levels sufficient to keep the pH of the endosomes at or about 5.5 or higher throughout the administration of the immunotoxin and for as long thereafter as free immunotoxin is present in the brain tissue. Such determinations can be made accurately from animal models (for example, by administering labeled immunotoxin and determining how much remains unbound to brain cells at different time points) and in vitro studies of endosomal pH. The time free immunotoxin is present in the brain will vary according to the dose given and particular targeting moiety used. The receptor, antigen, or ligand targeted by different targeting moieties varies, and is generally expected to correlate with the time free immunotoxin can be expected to be present. The transferrin receptor, for example, cycles some seven times per minute; it can be assumed, therefore that free immunotoxin is rapidly taken up by surrounding glioma cells. Immunotoxins directed to antigens on cell surfaces may have slower cycling times, and correspondingly longer times in which they are free (that is, unattached to a target cell or endocytosed into a target cell). Uptake times are commonly determined by standard in vitro assays using immunotoxins labeled in a manner which permits detection of the immunotoxin either within the cell or, after removal of the culture medium, detection of the immunotoxin present after the cells have been lysed.

Administration dosages and schedules can be determined by standard techniques well known in the field. See, e.g., Remingtons' Pharmaceutical Sciences, Gennaro, A., ed. Mack Publishing Co., Easton Pa. ($17^{th}$ Ed., 1985). The administration and dosing of a number of endosomal pH-raising agent is well known in the art since they have been used for years as anti-malarial agents and have been used as well to treat rheumatoid arthritis and lupus erythmatosus. See, e.g., Goodman and Gilman, supra at page 970. If desired, practitioners can, however, also determine how long to administer the endosomal pH-raising agent by analogy to the animal distress assays discussed in the Examples. If the animal starts to show signs of distress, it is an indication that the dosage of the endosomal pH-raising agent is not sufficient at that point in time and needs to be increased.

Drugs administered orally take a period of time to reach protective levels in the circulation. Typically, agents such as oral chloroquine which require time for plasma levels to build up are preferably administered 1 to 24 hours in advance of the administration of the immunotoxin to the brain so that there is time for the plasma levels of the agent to reach adequate levels (time for build-up of plasma levels is determined routinely during pre-clinical and Phase I testing). Since chloroquine reaches its maximum blood levels about 3 to 5 hours after oral administration, it is desirable to administer the chloroquine 3 to 5 hours before the immunotoxin is introduced so that there are high concentrations of the drug in the circulation during the time the immunotoxin is administered and for a time thereafter. Chloroquine, other lysosomotrophic amines, or an agent such as a proton ionophores or a blocker of the vacuolar H+ ATPase inhibitors can if desired be administered well prior to the administration of the immunotoxin so long as the level of the lysosomotrophic amine or other agent in the vascular endothelial cells serving the brain remains sufficient to provide them with the desired degree of protection from the immunotoxin during the time the immunotoxin is present.

Chloroquine can be administered in dosages ranging from about 10 mg/kg to about 55 mg/kg. In more preferred embodiments, the dosage ranges from about 20 mg/kg to about 45 mg/kg. The dosages tested thus far have been on the high end of this range. The practitioner can, however, readily determine in an animal model whether a particular dose is sufficiently protective by using distress assay set forth in the Examples. Similarly, appropriate doses of other agents, such as monensin or bafilomycin A can be determined by the distress assay.

If chloroquine is used, oral administration is generally preferred to parenteral administration. While chloroquine is considered an exceptionally safe drug in appropriate doses, when administered parenteraly, transiently lethal doses can occur due to its slow exit from the compartment into which it is administered. Thus, if administered by i.v., for example, it should be administered in a slow, continuous infusion, and if administered by subcutaneous or intramuscular routes, it should be given in small divided doses. See, e.g., Goodman and Gilman, supra, at page 971.

Administration of the chloroquine or other lysosomotrophic amine can also be commenced during the administration of the immunotoxin, or even after administration of the immunotoxin is ended. This is less desirable than administering the lysosomotrophic amine before or during administration of the immunotoxin, however, administration of the lysosomotrophic amine at any time while there is still immunotoxin present will still be of more benefit in protecting vascular endothelial cells than having no lysosomotrophic amine present at all.

EXAMPLES

Example 1

Materials and Methods

Cell Lines and Animals

The U251 human glioblastoma cell line and 9L rat gliosarcoma cell line were purchased from the American Type Culture Collection (Manassas, Va.). Both cell lines were grown in DMEM media supplemented with 10% FCS and maintained at 37° C. in a 5% $CO_2$ environment. Animal experiments were performed with male Fisher 344 rats (Taconic), 20–25 weeks of age, with a body weight ranging from 250 to 300 g and NIH nu/nu female mice 4–6 weeks of age, which were cared for in accordance with NIH guidelines.

DT, Tf-CRM107, and Chloroquine

DT was purchased from List Biologicals (Campbell, Calif.). Preparation of the DT mutant CRM107 and its conjugation to human Tf were performed as described previously (Johnson, V. G. et al., *J. Biol Chem.,* 263:1295–1300 (1988)). The toxin and Tf were linked by a thioether bond. Toxins and chloroquine were dissolved in PBS for in vitro experiments and in 0.9% physiological saline for in vivo experiments.

Tf-R Expression.

The mouse monoclonal anti-Tf-R antibody was purchased from ZYMED Laboratories (San Francisco, Calif.). This antibody (H68.4) is specific to residues 3–28 of the human Tf-R N-terminal tail and cross-reacts with rat Tf-R. The normal cerebrum, cerebellum, pons, medulla, and cervical segment of the spinal cord were removed from rats, and tumors were removed from rats bearing 9L brain tumors 14 days after tumor inoculation and frozen immediately in precooled isopentane with dry ice. The frozen tissues were homogenized with 1% Triton X-100 in PBS and centrifuged at 800×g, and the supernatant was saved. The protein concentration of each tissue sample was determined by the BCA protein assay kit (Pierce, Rockford, Ill.). Equal quantities of protein were separated on 4–12% Tris-Glycine Gel (Novel Experimental Technology, San Diego, Calif.) with an equal volume of Tris-Glycine SDS sample buffer 2× (NOVEX). The proteins separated by PAGE were electoblotted onto Immobilon PVDF membranes (Millipore, Mass.) using TRNSBLOT (Bio-Rad Laboratories, Hercules, Calif.). After blocking with 0.05% Tween 20 (Sigma) in PBS (pH 7.4) containing 5% FCS, the membranes were incubated with the primary antibodies for 1 h at room temperature. The membranes were then washed and incubated with horseradish peroxidase conjugated sheep antimouse IgG antibody (Amersham Pharmacia Biotech, Inc., Piscataway, N.J.). After thorough washing, the immunoreactive proteins were visualized by the ECL system (Amersham) according to the manufacturer's directions.

In vitro Cytotoxicity Assay

The toxicity of Tf-CRM107 to U251MG cells after chloroquine treatment was studied using [$^{14}$C]leucine incorporation as a measure of protein synthesis, as reported previously (Johnson, V. G. et al., *J. Biol Chem.,* 263:1295–1300 (1988)). Briefly, after U251MG cells were incubated with leucine-free RPMI 1640 for 6 h, chloroquine was added and incubated for 1 h. Several doses of Tf-CRM 107 ($7\times10^{-15}$ to $7\times10^{-8}$ M) were then added; 12 h later, 1 $\mu$Ci of [$^{14}$C]leucine was added, incubation was continued for 1 h, and then the cells were harvested. All cytotoxicity assays were performed three times. The results were expressed as a percentage of [$^{14}$C]leucine incorporation in mock-treated control cultures and were expressed as means±SE.

Maximum Tolerated Dose ("MTD") Assessment After anesthesia (i.p. injection of 80 mg/kg ketamine and 12 mg/kg xylazine), rats were placed in a stereotactic frame. A midline sagittal incision was made, and a dental drill was used to place a burr hole 3 mm lateral and 1 mm anterior to the bregma. Toxins were infused for MTD determination in a volume of 5 $\mu$l intracerebrally into rats at 1 $\mu$l/min, using a 10-$\mu$l Hamilton syringe. DT was given to achieve total doses of 00.025–0.2 $\mu$g, and Tf-CRM107 was given to achieve total doses of 0.1–0.5 $\mu$g. The rats received i.p. injections of either chloroquine (45 mg/kg; n=41) or vehicle (0.9% physiological saline; n=39) 5 min before intracerebral injection and once each day for 5 consecutive days. We observed all rats for at least 14 days. If animals showed signs of distress (lethargy, neurological deficit, or inability to obtain food and water), they were euthanized and decapitated, and the brains were removed immediately for histology. We considered the maximum dose of toxin injected intracerebrally that did not cause distress to be the MTD.

MRI

MRI was performed on rats under anesthesia (i.p. injection of 80 mg/kg ketamine and 12 mg/kg xylazine) to detect brain damage.

For toxicity measurement under conditions of infusion identical to MTD measurements, MRI was performed 3 days after injection with 0.4 $\mu$g of Tf-CRM107 (1 $\mu$l/min). The protocol used on these images was spin-echo multislice done on a GE Omega 2 Tesla horizontal bore instrument with 4 Gauss/cm shielded gradients. The T1-weighted image was taken with a TE/TR of 20/500 ms with a total scan time of 8.5 min. The T2-weighted images were taken with a TI/TR of 80/1500 ms with a total scan time of 51 min. Each of these slices had an in-lane digital resolution of 390 $\mu$m and 2-mm slice thickness.

To detect complete blocking of the toxicity of Tf-CRM107 by chloroquine in normal brain and to best model the infusion method used in clinical trials (CED), 0.05 $\mu$g of Tf-CRM107 in 5 $\mu$l were infused at 0.1 $\mu$l/min with a pressure gradient maintained using a syringe pump (Harvard Apparatus, S. Natick, MA), and the MRI was performed 14 days after infusion. The protocol used on these images was spin-echo multislice done on a Varian Inova 4.7 Tesla horizontal bore instrument with 15 gauss/cm shielded gradients. These T2-weighted images were taken with a TE/TR of 80/2000 ms; slice thickness was 1 mm with 1.5 mm between slice centers. Each of these slices had an in-lane digital resolution of 390 um.

Tumor Model

Solid U251MG human glioma tumors were grown by injecting $10^7$ cultured U251 MG cells s.c. into the flanks of nude mice. Palpable tumors were detected after 4–5 weeks and reached 0.4–0.6 cm in diameter. Tumor size was evaluated by measuring two perpendicular diameters with Vernier calipers and using the formula ½ $LW^2$, where L is the longest diameter and W is the diameter perpendicular to L. Groups of five nude mice with established U251 MG flank tumors were randomly assigned to receive intratumoral injections with 100 $\mu$l of either PBS or Tf-CRM107 (100 $\mu$g/ml; total dose, 10 $\mu$g) with or without chloroquine treatment. The mice received i.p. injection of either chloroquine (45 mg/kg; n=5) or vehicle (0.9% physiological saline; n=5) 5 min before intratumoral injection of Tf-CRM107 and once a day for 4 consecutive days at the same dose. Tumor volume, assessed for 10 days, was represented as a percentage of initial volume and expressed as a mean±SE.

Example 2

Chloroquine Increases MTD of, and Decreases Vascular Damage Due to, Tf-CRM107

Tf-R levels in different regions of normal rat brain were compared with the Tf-R level in 9L brain tumors. The Tf-R was detected as a homodimer (180 kDa) on Western blots. Normal brain (cerebrum, cerebellum, pons, medulla, and cervical segment of the spinal cord) expressed Tf-R with some variation in magnitude among different regions. The pons expressed particularly low levels of Tf-R, possibly reflecting the lower capillary density in white matter than gray matter. 9L brain tumors 14 days after inoculation into rat brains were also examined. The degree of expression of Tf-R in 9L tumors was higher than that normal CNS.

When 5 $\mu$l of Tf-CRM107 were infused into normal brain at 1 $\mu$l/min, total dose of 0.025 $\mu$g or more caused brain damage such as necrosis and encephalomalacia detected by histology by day 14 after infusion. These results were consistent with our previous reports (Laske, D. W. et al., *J. Neurosurg.*, 80:520–526 (1994)).

Tf-CRM107 toxicity to rat brain was examined by MRI. MRI of rat brains 3 days after intracerebral injection with 0.4 $\mu$g of Tf-CRM107 revealed a mass lesion with two components of different signal intensities in the right frontal lobe. The central component was isointense on the T-1 weighted MRI and low intensity on the Ts-weighted MRI. These MRI patterns are consistent with intact RBC's containing deoxyhemoglobin after hemorrhage. The outer component was low intensity on the T1-weighted MRI and high intensity on the T2-weighted MRI, indicating edema with the large occupational area representing hemorrhage and involved edema. Histology of the lesion showed hemorrhage with necrosis, tissue loss, and invasion by macrophages. These changes in the brain detected by MRI and histopathology indicate that Tf-CRM107 causes vascular damage. Tf-CRM107 at high doses may bind to Tf-Rs on capillary endothelial cells and cause thrombosis and then hemorrhagic infarction, or it may directly cause hemorrhage as a result of endothelial injury.

Chloroquine is known to block the toxicity of DT in vitro (Leppla, S. et al., *J. Biol. Chem.*, 255:2247–2250 (1980)). We found chloroquine in vitro blocked the toxicity of Tf-CRM107 10–100-fold, and at a concentration of Tf-CRM107 of $7 \times 10^{-11}$ M, cells were completely protected by 10 $\mu$m chloroquine (FIG. 1A).

Rats receiving 0.4 $\mu$g of Tf-CRM107 exhibited clinical signs of toxicity. We postulated that systemic delivery of chloroquine may protect the CNS vasculature from Tf-CRM107 and decrease CNS toxicity in vivo. We examined the MTD of Tf-CRM107 with and without chloroquine administration. After intracerebral injection with 0.2 ug of Tf-CRM107, no remarkable symptoms were observed in five of five rats. However, five (71%) of the seven rats that received 0.3 $\mu$g of Tf-CRM107 showed signs of distress around day 6 after injection. Five of five rats that received 0.4 $\mu$g of Tf-CRM107 died around day 4. If rats received chloroquine (45 mg/kg) following injection with 0.3 $\mu$g of Tf-CRM107, however, zero of five animals showed signs of distress. Although 0.4 $\mu$g of Tf-CRM107 with chloroquine caused signs of distress in four (80%) of five animals, chloroquine increased the survival rate and changed the MTD of Tf-CRM107 from 0.2 $\mu$g to 0.3 $\mu$g (FIG. 1B). Thus, systemic chloroquine protects animals from intracerebral toxicity due to Tf-CRM107.

Intracerebral infusion with 0.05 $\mu$g of Tf-CRM107 (10 $\mu$g/ml) caused histological brain damage (i.e., necrosis) in the right frontal lobe by day 14. Toxicity at this dose was detected as a high intensity lesion on T2-weighted MRI. Systemic chloroquine administration (45 mg/kg, administered i.p. for 5 days) completely blocked the brain damage caused by 0.05 $\mu$g of Tf-CRM107 at day 14 in rat that received 0.9% physiological saline instead of chloroquine (n=3). Tr-CRM107 was microinfused at 0.1 μl/min using a syringe pump.

Example 3

Chloroquine Administered Systemically Does Not Impair Toxicity of Immunotoxins Administered Into the Brain One object of the studies herein was to determine whether the BBB limits the amount of chloroquine that can pass into the cerebral fluid, and therefore prevents enough chloroquine from entering the brain to block the antitumor activity of immunotoxins such as Tf-CRM107. The brains of rats and mice are too small to accurately model brain tumor infusion; therefore, we used a surrogate measure of chloroquine entry into the brain. To assess whether enough chloroquine crosses the BBB to inhibit antitumor activity of Tf-CRM107, we used native DT that has a similar sensitivity to chloroquine (Johnson, V. G. et al., *J. Biol Chem.*, 263:1295–1300 (1988); Leppla, S. et al., *J. Biol. Chem.*, 255:2247–2250 (1980)). In contrast to Tf-CRM107, which in the CNS targets endothelial cells, in the rat brain, DT is selectively toxic to neurons (Agarwal, S. C., and Pryce, D. M., *J. Path. Bact.*, 78:171–177 (1959)); thus, the cell type targeted by DT is on the same side of the BBB as are brain tumor cells. We checked the effect of systemic chloroquine on the survival rate of rats injected intracerebrally with DT. Although none of four rats that received 0.1 μg of DT showed signs of distress, all four rats that received 0.2 μg of DT showed signs of distress around day 5. When chloroquine was injected i.p. at 45 mg/kg in addition to 0.2 μg of intracerebral DT, all four animals showed signs of distress around day 5. Thus, i.p. injection of chloroquine does not block toxicity of intracerebral DT. Although i.p. injection of chloroquine appears to reach and protect the brain vasculature from Tf-CRM107, it does not protect the CNS neurons from DT.

Contrast-enhancing brain tumors may have a partially defective BBB, and this may allow enough chloroquine into the brain tumor to block Tf-CRM107 efficacy. This hypothesis was tested, using a "worst-case scenario" of leaky tumor vasculature in the periphery. Tf-CRM107 was injected into U251 tumors grown in the flanks of nude mice with and without i.p. injection of chloroquine. Intratumoral injection of Tf-CRM107 significantly inhibited tumor growth compared with PBS (P<0.01), and i.p. injection of chloroquine at 45 mg/kg caused little or no blocking of the efficacy of Tf-CRM107 against the s.c. tumor.

Tf-CRM107 infused intratumorally using high-flow interstitial microinfusion into patients with recurrent malignant brain tumors caused at least a 50% reduction in tumor volume in 8 of 15 patients (Laske, D. W. et al., *Nat. Med.*, 3:1362–1368 (1997)). To improve on this outcome, we have considered ways to increase the dose of Tf-CRM107 safely to more effectively eradicate tumor cells. In that clinical study peritumoral, focal brain injury occurred in all patients who received 40 μg of Tf-CRM107 at 1 μg/ml. Histological analysis of biopsies revealed thrombosed cortical venules and/or capillaries. Thus, dose-limiting toxicity associated with intratumoral Tf-CRM107 infusion in humans is consistent with brain capillary endothelial damage. Tf-Rs are expressed on endothelial cells in normal brain (Jeffries, W. A. et al., *Nature*, 312:162–163 (1984)). Although most Tf-Rs appear on the capillary lumen (Jeffries, W. A. et al., supra), they may cycle through the cell to the abluminal side where they may bind intracerebral Tf-CRM107. High doses of Tf-CRM107 may cause hemorrhagic infarction following diffuse vessel thrombosis or cause hemorrhage directly after binding to Tf-Rs on capillary endothelial cells. Intracerebral infusion of Tf-CRM107 into rat brains at doses ≧0.025 μg caused CNS damage detected by both histology and MRI. We detected MRI damage at 40 μg (roughly 0.8 μg/kg) of Tf-CRM107 in humans and at 0.025 μg (roughly 0.1 μg/kg) in rats. This discrepancy in MTD between rats and humans may in fact be due to differences in the infusion rate or infusion volume relative to the size of the brain. Because it may be implausible to continuously infuse rats over 5 days to precisely model infusion in humans, we have not been able to compare MTD directly between rats and humans by the same delivery technique.

We sought to overcome the dose-limiting toxicity of Tf-CRM107. To protect normal capillaries from Tf-CRM107, we identified a drug that would block Tf-CRM107. DT has a series of hydrophobic domains (Eisenberg, D. et al., *J. Mol. Biol.*, 179:125–142 (1984); Oh, K. J. et al., *Science* (Washington D.C.), 273:810–812 (1996)) that insert into membranes when exposed to the low pH present in endosomes and lysosomes (Sandvig, K., and Olsnes, *J. Biol. Chem.*, 256:9068–9076 (1981); Donovan, J. J. et al., *Proc. Natl. Acad. Sci. USA*, 78:172–176 (1981); Sandvig, K., and Olsnes, S. *J. Cell Biol.*, 87:828–832 (1980); Draper, R. K., and Simon, M. I., *J. Cell Biol.*, 87:849–854 (1980)). Chloroquine blocks the toxicity of DT by increasing and neutralizing endosomal pH (Kim, K., and Groman, N. B., *J. Bacteriol.*, 90:1552–1556 (1965); Leppla, S. et al., *J. Biol. Chem.*, 255:2247–2250 (1980)) and blocks the toxicity of Tf-CRM107. Chloroquine also can increase the survival of rats after intracerebral Tf-CRM107 infusion and prevents the MRI changes associated with toxicity. The high intensity signal on T2-weighted MRI may reflect the histological damage due to thrombosed capillaries or petechial hemorrhage. Generally speaking, T2-weighted MRI is very sensitive for detection of this type of brain damage. Chloroquine treatment protected animals from this damage caused by Tf-CRM107.

We considered the extent to which chloroquine crosses the BBB. The most important factors determining drug delivery from blood into CNS are lipid solubility, molecular mass and charge. Seelig, A. et al., *Proc. Natl. Acad. Sci. USA*, 91:68–72 (1994). The normal BBB inhibits the passage of water-soluble drugs with a molecular mass greater than 180 Da. Chloroquine (516 Da) is freely soluble in water and insoluble in alcohol, benzene, chloroform, or ether. Our experiments revealed that chloroquine did not change the MTD of intracerebrally injected DT and did not reduce the histological rain damage in rates that received DT. On the other hand, chloroquine blocked the toxicity of intracerebrally injected Tf-CRM107. The different sensitivities of intercerebral DT and Tf-CRM107 to systemic chloroquine supports the model that Tf-CRM107 is specifically targeting capillary endothelial cells. Chloroquine does not cross the BBB to a degree sufficient to block DT and thus should not block the antitumor efficacy of Tf-CRM107 injected intracerebrally.

We directly investigated whether chloroquine inhibited the antitumor efficacy of Tf-CRM107. The BBB is intact at the proliferating edges of malignant brain tumors and in regions of infiltrated brain but is more leaky in the center (Yamada, K. et al., *J. Neurosurg.*, 57:394–398 (1982)). In practice, clinical studies with computed tomography reveal that BBB permeability is variable in brain tumors (Chamberlain, M. C. et al., *Neurology*, 38:1371–1374 (1988)). We found that chloroquine treatment causes little or no blocking of the efficacy of intratumoral Tf-CRM107 even in s.c. tumors entirely lacking the BBB. The BBB should even further minimize chloroquine access to brain tumors. It appears that chloroquine may block the toxicity to the vasculature with little effect on the antitumor efficacy of Tf-CRM107 in brain.

Although some side effects are known, chloroquine has generally been considered safe and may be taken p.o. Eleven healthy volunteers given 300 mg of chloroquine as a single dose i.v. infusion complained only of subjective side effects, such as difficulties with swallowing and accommodation, dilopia, and fatigue during i.v. infusion; no effects were seen on the electrocardiogram, mean arterial blood pressure, or pulse rate (Gustaffsson, L. L. et al., *Br. J. Clin. Pharmacol.*, 15:471–479 (1983)). Patients unable to take oral doses might be given chloroquine by slow i.v. infusion or by s.c. or i.m. injection (Aderounmu, A. F. et al., *Br. J. Clin. Pharmacol.*, 22:559–564 (1986)).

Computed tomography and MRI studies using i.v. contrast enhancement define the location of brain tumors because contrast media leaks from regions lacking an intact BBB. Although tumor resection is performed as precisely as possible according to scans of the enhancing lesion, the proliferating edge of tumor does not contrast enhance because the BBB remains intact and tumor cells are known to invade centimeters beyond the enhancing lesion (Scherer, H. J., *Brain*, 63:1–35 (1940); Greene, G. M. et al., *J. Neurosurg.*, 71:494–497 (1989); Kelly, P. J. et al., *J. Neurosurg.*, 66:865–874 (1987)). After surgical resection, this residual tumor in areas with an intact BBB is the major factor underlying the failure of current treatments of these patients. Tf-CRM107 may ultimately be best used soon after surgery to treat this region of tumor infiltrated brain after resection of all contrast-enhancing volume. In this situation, chloroquine should be greatly restricted from the tumor by the intact BBB. The i.v. injection of chloroquine during intracerebral infusion of Tf-CRM107 may protect the vasculature, permitting less toxicity to the brain while allowing greater doses of Tf-CRM107 to be delivered to tumor to further improve the response rate of this new cancer therapy.

All publications and patents mentioned in this specification are herein incorporated by reference into the specification to the same extent as if each individual publication or patent was specifically and individually indicated to be incorporated herein by reference. Citation of various references in this document does not constitute an admission that any particular reference is "prior art" to the invention.

What is claimed is:

1. A method of decreasing toxicity of an immunotoxin administered into a brain to a vascular endothelial cell in the brain, the method comprising systemically administering an endosome pH-raising agent in an amount sufficient to decrease toxicity of the immunotoxin to the vascular endothelial cell.

2. A method of claim 1, wherein the endosome pH-raising agent is selected from the group consisting of a lysosomotrophic amine, a proton ionophore, and a vacuolar H+ ATPase inhibitor.

3. A method of claim 2, wherein the proton ionophore is monensin.

4. A method of claim 2, wherein the vacuolar H+ ATPase inhibitor is bafilomycin A.

5. A method of claim 1, wherein said immunotoxin comprises a toxic moiety selected from the group consisting of a mutated Pseudomonas exotoxin (PE) and a mutated diphtheria toxin (DT).

6. A method of claim 5, wherein the toxic moiety is selected from the group consisting of PE4E, PE35, PE38, and PE40.

7. A method of claim 5, wherein the toxic moiety is selected from the group of a diphtheria toxin (DT) with a deletion of all or some of the native receptor-binding domain which results in reduced non-specific binding or toxicity compared to wild-type DT, a diphtheria toxin with a substitution of an amino acid for serine at position 508 which results in reduced non-specific binding or toxicity compared to wild-type DT, a diphtheria toxin with a substitution of an amino acid for serine at position 525 which results in reduced non-specific binding or toxicity compared to wild-type DT, and a diphtheria toxin with a substitution of an amino acid other than serine for serine at position 508 and of an amino acid other than serine for serine at position 525, which substitutions result in reduced non-specific binding or toxicity compared to wild-type DT.

8. A method of claim 7, wherein the toxic moiety is a mutated diphtheria toxin wherein phenylalanine is substituted for serine at position 525 ("CRM107").

9. A method of claim 7, in which the toxic moiety is a diphtheria toxin with a deletion of the native receptor-binding domain commencing at an amino acid residue selected from residue 388 and residue 389.

10. A method of claim 5, wherein the immunotoxin is Tf-CRM107.

11. A method of claim 10, wherein the endosome pH-raising agent is chloroquine.

12. A method of decreasing toxicity of an immunotixin to a vascular endothelial cell having a lumenal surface and an ablumenal surface without decreasing toxicity of the immunotoxin to a tumor cell proximal to the ablumenal surface of said vascular endothelial cell, said method comprising contacting the lumenal surface, but not the ablumenal surface, of said vascular endothelial cell with an endosome pH-raising agent without contacting said tumor cell with said endosome pH raising agent.

13. A method of claim 12, wherein the endosome pH-raising agent is selected from the group consisting of a lysosomotrophic amine, a proton ionophore, and a vacuolar H+ ATPase inhibitor.

14. A method of claim 13, wherein the proton ionophore is monensin.

15. A method of claim 13, wherein the vacuolar H+ ATPase inhibitor is bafilomycin A.

16. A method of claim 12, wherein said contacting is in vivo.

17. A method of claim 12, wherein said immunotoxin comprises a toxic moiety selected from the group consisting of a mutated Pseudomonas exotoxin (PE) and a mutated diphtheria toxin (DT).

18. A method of claim 17, wherein the toxic moiety is selected from the group consisting of PE4E, PE35, PE38, and PE40.

19. A method of claim 17, wherein the toxic moiety is selected from the group of a diphtheria toxin (DT) with a deletion of all or some of the native receptor-binding domain which results in reduced non-specific binding or toxicity compared to wild-type DT, a diphtheria toxin with a substitution of an amino acid for seine at position 508 which results in reduced non-specific binding or toxicity compared to wild-type DT, a diphtheria toxin with a substitution of an amino acid for serine at position 525 which results in reduced non-specific binding or toxicity compared to wild-type DT, and a diphtheria toxin with a substitution of an amino acid other than serine for serine at position 508 and of an amino acid other than serine for serine at position 525, which substitutions result in reduced non-specific binding or toxicity compared to wild-type DT.

20. A method of claim 19, wherein the toxic moiety is a mutated diphtheria toxin with a substitution of phenylalanine for serine at position 525 (CRM107).

21. A method of claim 19, wherein the immunotoxin is transferrin (Tf)-CRM107.

22. A method of claim 21, in which the toxic moiety is a diphtheria toxin with a deletion of the native receptor-binding domain commencing at an amino acid residue selected from residue 388 and residue 389.

23. A method of claim 12, wherein said vascular endothelial cell is in a brain of a mammal.

24. A method of claim 23, wherein said mammal is a human.

25. A method of claim 24, wherein the immunotoxin is administered directly into the brain and the endosome pH-raising agent is administered systemically.

26. A method of claim 25, wherein the immunotoxin is Tf-CRM107.

27. A method of claim 26, wherein the endosome pH-raising agent is chloroquine.

28. A method of decreasing toxicity of an immunotoxin administered into a brain to a vascular endothelial cell in the brain, the method comprising systemically administering a lysosomotrophic amine in an amount sufficient to decrease toxicity of the immunotoxin to the vascular endothelial cell.

29. A method of claim 28, wherein the lysosomotrophic amine is selected from the group consisting of chloroquine, hydrochloroquine, mefloquine, and a congener of chloroquine.

30. A method of claim 28, wherein said immunotoxin comprises a toxic moiety selected from the group consisting of a mutated Pseudomonas exotoxin (PE) and a mutated diphtheria toxin (DT).

31. A method of claim 30, wherein the toxic moiety is selected from the group consisting of PE4E, PE35, PE38, and PE40.

32. A method of claim 30, wherein the toxic moiety is selected from the group of a diphtheria toxin (DT) with a deletion of all or some of the native receptor-binding domain which results in reduced non-specific binding or toxicity compared to wild-type DT, a diphtheria toxin with a substitution of an amino acid for serine at position 508 which results in reduced non-specific binding or toxicity compared to wild-type DT, a diphtheria toxin with a substitution of an amino acid for serine at position 525 which results in reduced non-specific binding or toxicity compared to wild-type DT, and a diphtheria toxin with a substitution of an amino acid other than serine for serine at position 508 and of an amino acid other than serine for serine at position 525, which substitutions result in reduced non-specific binding or toxicity compared to wild-type DT.

33. A method of claim 32, wherein the toxic moiety is a mutated diphtheria toxin wherein phenylalanine is substituted for serine at position 525 ("CRM107").

34. A method of claim 32, which the toxic moiety is a diphtheria toxin with a deletion of the native receptor-binding domain commencing at an amino acid residue selected from residue 388 and residue 389.

35. A method of claim 32, wherein the immunotoxin is Tf-CRM107.

36. A method of decreasing toxicity of an immunotoxin to a vascular endothelial cell having a lumenal surface and an ablumenal surface without decreasing toxicity of the immunotoxin to a tumor cell proximal to the ablumenal surface of said vascular endothelial cell, said method comprising contacting the lumenal surface, but not the ablumenal surface, of said vascular endothelial cell with a lysosomotrophic amine without contacting said tumor cell with said lysosomotrophic amine.

37. The method of claim 36, wherein the lysosomotrophic amine is selected from the group consisting of chloroquine, hydrochloroquine, mefloquine, and a congener of chloroquine.

38. A method of claim 36, wherein said contacting is in vivo.

39. A method of claim 36, wherein said immunotoxin comprises a toxic moiety selected from the group consisting of a mutated Pseudomonas exotoxin (PE) and a mutated diphtheria toxin (DT).

40. A method of claim 39, wherein the toxic moiety is selected from the group consisting of PE4E, PE35, PE38, and PE40.

41. A method of claim 39, wherein the toxic moiety is selected from the group of a diphtheria toxin (DT) with a deletion of all or some of the native receptor-binding domain which results in reduced non-specific binding or toxicity compared to wild-type DT, a diphtheria toxin with a substitution of an amino acid for serine at position 508 which results in reduced non-specific binding or toxicity compared to wild-type DT, a diphtheria toxin with a substitution of an amino acid for serine at position 525 which results in reduced non-specific binding or toxicity compared to wild-type DT, and a diphtheria toxin with a substitution of an amino acid other than serine for serine at position 508 and of an amino acid other than serine for serine at position 525, which substitutions result in reduced non-specific binding or toxicity compared to wild-type DT.

42. A method of claim 41, wherein the toxic moiety is a mutated diphtheria toxin with a substitution of phenylalanine for serine at position 525 (CRM107).

43. A method of claim 41, wherein the immunotoxin is transferrin (Tf)-CRM107.

44. A method of claim 43, in which the toxic moiety is a diphtheria toxin with a deletion of the native receptor-binding domain commencing at an amino acid residue selected from residue 388 and residue 389.

45. A method of claim 12, wherein said vascular endothelial cell is in a brain of a mammal.

46. A method of claim 45, wherein said mammal is a human.

47. A method of claim 46, wherein the immunotoxin is administered directly into the brain and the endosome pH-raising agent is administered systemically.

48. A method of claim 47, wherein the immunotoxin is Tf-CRM107.

* * * * *